United States Patent [19]

Micchelli et al.

[11] 3,973,901

[45] Aug. 10, 1976

[54] HAIR COLORING COMPOSITION CONTAINING A WATER-SOLUBLE CATIONIC POLYMER AND A PROCESS FOR USE THEREOF

[75] Inventors: Albert L. Micchelli, Middletown; Frank A. Nowak, Jr., Bound Brook; Gerard J. Legato, Stirling, all of N.J.

[73] Assignee: National Starch and Chemical Corporation, Bridgewater, N.J.

[22] Filed: June 18, 1975

[21] Appl. No.: 587,824

Related U.S. Application Data

[63] Continuation-in-part of Ser. No. 422,176, Dec. 6, 1973, abandoned.

[52] U.S. Cl. .................................... 8/10.1; 8/10; 8/41 R; 8/87; 8/88; 8/85 R; 424/DIG. 2; 424/70; 424/71
[51] Int. Cl.² .................................... A61K 7/13
[58] Field of Search .............. 8/10, 10.1, 85, 87, 8/88, 41 R

[56] References Cited
UNITED STATES PATENTS

| | | | |
|---|---|---|---|
| 2,138,763 | 11/1938 | Graves | 260/89.7 N |
| 2,694,688 | 11/1954 | Hughes | 260/89.7 N |
| 2,808,349 | 10/1957 | Melamed | 260/89.7 N |
| 2,979,491 | 4/1961 | Piloni | 260/89.7 N |
| 3,239,496 | 3/1966 | Jursich | 260/89.5 |
| 3,361,718 | 1/1968 | Fujimoto et al. | 260/49 |
| 3,372,149 | 3/1968 | Fertig et al. | 260/78.4 |
| 3,630,654 | 12/1971 | Rosenthal et al. | 8/10.1 |

*Primary Examiner*—Sam Rosen
*Assistant Examiner*—Vera C. Clarke

[57] ABSTRACT

A process for coloring hair and the hair coloring compositions employed therefor are disclosed. Said process essentially comprises treating the hair with an acid dye in the presence of an aqueous solution of a water soluble cationic polymer selected from the group consisting of water-soluble acid salts of aminoalkyl esters of homo- and copolymers of unsaturated carboxylic acids having from 3 to 5 carbon atoms. Said hair coloring composition essentially comprises an aqueous solution of a water-soluble acid salt of an aminoalkyl ester of a homo- or copolymer of said unsaturated carboxylic acids in combination with a small amount of an acid dye.

8 Claims, No Drawings

HAIR COLORING COMPOSITION CONTAINING A WATER-SOLUBLE CATIONIC POLYMER AND A PROCESS FOR USE THEREOF

This application is a continuation-in-part of co-pending application Ser. No. 422,176 filed on Dec. 6, 1973, now abandoned.

This invention relates to an improved process for coloring hair and an improved hair coloring composition. More particularly, this invention relates to (1) a process for coloring hair by treating the hair with an acid type dye in the presence of an aqueous solution of a water-soluble cationic polymer and (2) a hair coloring composition essentially comprising an aqueous solution of a small amount of a water-soluble cationic polymer in combination with a small amount of at least one acid type dye.

As is well known in the art, there are basically three types of dyes commonly used in the coloring or 'dyeing' of human hair. These types of dyes, i.e., permanent or oxidative, semipermanent, and temporary, are categorized according to the durability and longevity of the color imparted to the hair. In other words, the dyes are classified on the basis of their fastness to commerical shampooing, i.e., on the basis of the number of conventional washings they are capable of withstanding.

It is well known that permanent colors, i.e., those which employ low molecular weight, colorless intermediates such as p-aminophenol and p-phenylenediamine, are used in conjunction with hydrogen peroxide; and, that, due to their tremendous depth of coloring or extremely high degree of coverage, they are most widely used in commercial hair coloring preparations. It is also well known that certain inherent drawbacks remain with the use of permanent colors in hair coloring preparations. For instance, the use of potentially hazardous hydrogen peroxide is required. Also, since the permanent colors usually remain fast until the hair grows out, they are most difficult for a dissatisfied individual to remove. Hence there exists a need on the market for a means of coloring hair and for hair coloring preparations which, when utilized, are characterized by their abilities to readily overcome the problems so often encountered with permanent colors.

In order to be useful in the above described manner, any improved means for coloring hair and any composition designed theefor must not only be nonirritating and capable of remaining fast through a considerable number of washings but, also capable of producing the desired shade without noticeably staining the scalp and capable of leaving the hair in good condition.

It is, thus, an object of this invention to provide an improved process for coloring human hair. It is a further object of this invention to provide a means whereby certain non-oxidation colors having poor fastness to shampooing are rendered semipermanent. It is a still further object of this invention to provide hair coloring compositions which are devoid of any irritants and are capable of displaying improved fastness to shampooing.

These and various other objects and advantages of this invention will become apparent to the practitioner from the following description thereof.

We have now found the aforementioned problems are readily overcome by treating the hair with an acid dye, in an aqueous solution, in the presence of a water-soluble cationic polymer selected from the group consisting of water-soluble acid salts of non-quaternized aminoalkyl esters of homo- and copolymers of polymerizable unsaturated carboxylic acids having 3 to 5 carbon atoms.

We have also found that hair coloring compositions, comprising an aqueous solution of a small amount of one or more acid dyes in combination with a small amount of a cationic polymer selected from the group consisting of water-soluble acid salts of non-quaternized aminoalkyl esters of homo- and copolymers of polymerizable unsaturated carboxylic acids having 3 to 5 carbon atoms, may be prepared.

In both of the above mentioned aspects of this invention the hair is rendered more electropositive by the presence of a resin deposited from the cationic polymer on the hair fibers. That is to say, that the dye receptivity and the fastness of the applied dye are markedly improved due to the presence of the microscopically thin layer of polymer resin encasing the hair filaments.

Briefly, the novel hair coloring or dyeing process of this invention comprises the steps of (1) applying to the hair and uniformly massaging throughout the fibers thereof an aqueous solution comprising from about 0.1 to about 10.0 per cent, by weight, of the total solution of a resin depositing cationic polymer in the form of a water-soluble acid salt of a non-quaternized aminoalkyl ester of a polymer of an unsaturated carboxylic acid having 3 to 5 carbon atoms; (2) if desired, rinsing the hair with water and removing any excess polymer and water therefrom with a towel; and (3) uniformly applying to the hair an aqueous solution of from about 0.01 to about 1.0 per cent, by weight, of the total solution of an acid dye as described hereinafter, and then after a period of from 2–5 minutes rinsing and drying the hair.

As indicated, Step 2 of the above described process may be omitted. That is to say, as an alternate embodiment in the process of this invention, the rising of the cationic polymer treated hair is optional.

As a still further alternate embodiment in the process of this invention, Steps 1 and 3 may be carried out simultaneously with Step 2 again omitted. More specifically, if the practitioner desired to avoid both the three step and the two step processes described above, a one step process may be carried out by combining the cationic polymer of Step 1 with the acid dye of Step 3 in an aqueous solution at concentrations within the respectively prescribed ranges.

The novel hair coloring compositions of this invention essentially comprise aqueous solutions of (1) from about 0.1 to about 10.0 per cent, by weight, of the total solution of a resin depositing, cationic polymer in the form of an acid salt of a non-quaternized aminoalkyl ester of a polymer of an unsaturated carboxylic acid having 3 to 5 carbon atoms; and (2) from about 0.01 to about 1.0 per cent, by weight, of the total solution of at least one acid dye.

The novel, hair coloring compositions of this invention are prepared by merely dispersing the resin-depositing, cationic polymer and the acid dye in water with moderate agitation. When a homogeneous mixture of these two ingredients has been obtained, any optional ingredients may be added under appropriate conditions. For instance, the addition of a particular functional compound may require an initial temperature or pH adjustment to ensure complete solubilization. Also, it may be desired ultimately to adjust the pH level.

The pH adjusting agent and quantity to be used should be chosen to ensure maximum efficiency of the hair coloring composition and avoid damaging the hair or irritating the eyes or skin. A preferred pH range for the solutions prepared according to this invention is from 3.0-5.0. Since the initial pH level of the hair coloring compositions herein is usually between 2.5 and 7.0, it is preferred that weak acids such as citric acid, acetic acid, phosphoric acid, and the like and weak bases such as the alkanolamines, e.g., triethanolamine, diethanolamine, etc. be used as pH adjusting agents.

Among the various cationic polymers useful in the practice of this invention are included the mineral acid salts of the aminoalkyl esters of homo- and copolymers of unsaturated caboxylic acids having from 3 to 5 carbon atoms, for example, acrylic acid, crotonic acid, ethacrylic acid, fumaric acid, maleic acid and itaconic acid, and the aminoalkyl groups contain from 2 to 6 carbon atoms. Useful aminoalkyl groups include, for example, aminoethyl, N-methyl aminoethyl, N-ethyl aminoethyl, 2-aminopropyl and t-butyl aminoethyl, with the aminoethyl being preferred.

More specifically, the useful polymers include the salts of the aminoalkyl esters of (a) homopolymers of homopolymerizable unsaturated carboxylic acids having 3 to 5 carbon atoms (b) copolymers of copolymerizable mixtures of said acids, and (c) copolymers formed of unsaturated carboxylic acids having 3 to 5 carbon atoms and at least one copolymerizable ethylenically unsaturated comonomer selected from the group consisting of vinyl acetate and vinly propionate; vinyl methyl ether and vinyl ethyl ether; the $C_1$–$C_8$ alkyl esters of maleic and fumaric acids and the $C_1$–$C_8$ alkyl half esters of maleic and fumaric acids, for example, diethyl fumarate, dioctyl fumarate, dibutyl maleate, dioctyl maleate, monobutyl maleate, monomethyl fumarate, and monooctyl fumarate; amides of acrylic and methacrylic acids, for example, acrylamide, N-methyl acrylamide, and methacrylamide; and the $C_1$–$C_{18}$ alkyl and $C_2$–$C_4$ hydroxyalkyl esters of acrylic and methacrylic acids. Specific examples of the latter class of comonomers includes methyl acrylate, ethyl acrylate, butyl acrylate, octyl acrylate, dodecyl acrylate, stearyl acrylate, hydroxyethyl acrylate, hydroxypropyl acrylate, as well as the corresponding methacrylate esters. Preferred comonomers include the amides and the $C_1$–$C_{18}$ alkyl and $C_2$–$C_4$ hydroxyalkyl esters of acrylic and methacrylic acids.

The latter copolymers will be prepared with at least about 25 mole percent — preferably, at least 80 mole percent — of the unsaturated carboxylic acid.

With regard to the preparation of cationic polymers useful in the practice of this invention, the practitioner will recognize that such materials may be commercially available or may normally be synthesized either (1) by polymerizing monomers which have the functional aminoalkyl ester groups attached or (2) by subsequently affixing said groups to a base polymer such as the homopolymer of an ethylenically unsaturated carboxylic acid or a copolymer formed with at least one ethylenically unsaturated carboxylic acid and one or more copolymerizable comonomers. For example, the first method would typically involve the homopolymerization of one of the following: t-butylaminoethyl methacrylate, dimethylaminoethyl methacrylate, or the copolymerization of any one of the foregoing compounds with one or more of the above-mentioned copolymerizable comonomers. Such methods are disclosed in, inter alia, Piloni, U.S. Pat. No. 2,979,491; P. L. deBenneville, U.S. Pat. No. 2,744,884; and in Mowry et al., U.S. Pat. No. 2,625,471. The second method wherein the functional, aminoalkyl ester groups are affixed to the base polymer may be carried out according to the process taught in, inter alia, assignee's Fertig et al., U.S. Pat. No. 3,372,149. Regardless of the means of synthesis selected, a well-known free radical polymerization procedure is usually entailed. The cationic polymers produced thereby may have molecular weights ranging from about 5,000 to about 250,000. These compounds, upon utilization in accordance with this invention, are all characterized by their ability to impart the desired improved dye acceptability to the hair fibers.

Among the dyes useful in the process for coloring hair and in the preparation of the hair coloring products of this invention are included those compounds commonly referred to as the acid dyes. Aside from their structures and actual colors, these dyes may diffe significantly one from another from the viewpoint of dyeing properties, shade, and fastness. Though, due to their structural characteristics, the simple acid dyes are usually subclassified as chemical types, e.g., azo, anthraquinone, azine, xanthene, triphenylmethane, etc., they all contain sulfonic or carboxylic or other acid groups. Examples of such dyes are those which meet federally imposed Food, Drug, and Cosmetic (F. D. & C.) standards (Color Index numbers in parentheses), e.g., Acid Orange 10 (16230), Acid Violet 1 (17025), Acid Blue 1 (42045), Acid Green 3 (42084), F. D. & C. Blue 2 (73015), F. D. & C. Yellow 5 (19140), F. D. & C. Yellow 6 (15985), F. D. & C. Red 2 (16185), F. D. & C. Red 3 (54430), F. D. & C. Red 4 (14700), F. D. & C. Brown 1 (20170), F. D. & C. Green 3 (42053), F. D. & C. Green 5 (61570), F. D. & C. Orange 11 (45425), and other acid type dyes approved for cosmetic uses.

The practitioner will recognize that the actual concentration of any particular cationic polymer used in a given hair coloring composition encompassed within this invention may vary within the prescribed range, for many reasons. For example, the maximum usable concentration will depend on the nature and molecular weight of the polymer, its compatibility with the dye and any optional ingredients used, the degree of pH adjustment, if required, and the neutralizing agent utilized.

In the practice of this invention, it is preferred that in both the process and the compositions the resin depositing, cationic polymer used be the phosphate salt of one of the following: poly(aminoethyl acrylate) or poly(aminoethyl-hydroxypropyl acrylate) or a terpolymer of an aminoalkyl ester of an ethylenically unsaturated carboxylic acid, an amide of an ethylenically unsaturated carboxylic acid, and a hydroxyalkyl ester of an ethylenically unsaturated carboxylic acid wherein said cationic polymer has a molecular weight between about 25,000 and about 250,000 and is used at a concentration ranging from about 0.3 to about 0.8 per cent, by weight, of the total solution.

With regard to the concentration of the acid dye component employed in both the process and the preparations for coloring hair, in accordance with this invention, it is preferred that the amount range from about 0.1 to about 1.0 per cent, by weight, of the total solution. Obviously, since the particular dye or plurality of dyes to be used will depend on the desired shade, the selection of a preferred dye or combination of dyes is left to the practitioner.

Since some of the ingredients employed in the practice of this invention tend to support bacterial growth, a small amount of a preservative should be added to prevent such microbial growth. Though other well known preservatives and bactericides such as formaldehyde may be employed, we prefer to use the lower molecular weight alkyl p-hydroxybenzoates.

Optional ingredients may be incorporated into the hair coloring compositions of this invention in order to modify certain properties thereof. Among these additives may be included: surface active materials, solvents, thickeners, and, at times, dye carriers or boosters, protein hydrolyzates and other protein derivatives, cholesterol derivatives, perfumes, and ultraviolet light absorbers. The resin depositing polymer and the acid dyes show little or no tendency to react with such additives.

The resinous films deposited on the hair by the aqueous solutions of cationic polymers used in the novel process and compositions herein possess good antistatic properties, adhere well to the hair, do not become tacky, and, most of all, render the hair fibers more receptive to the dye applied thereto. Said films are transparent, glossy, and when subsequently dried with the dye intimately associated therewith, flexible and strong. Therefore, it should be noted that the resin depositing cationic polymers utilized in the practice of this invention are also capable of imparting outstanding manageability and, at times, generally improved conditioning properties when optional conventional ingredients are incorporated therewith.

The resulting hair coloring compositions of this invention, when utilized in a conventional manner, exhibit all of the characteristics required of such products.

Regardless of whether the dye, in its aqueous form, is applied separately or in combination with the cationic polymer, it is capable of diffusing from the bulk solution to the fibers of the swollen hair. Though it is not known whether or not the dye molecules, upon penetrating said fibers, react with themselves or otherwise, the resulting shade is nonetheless capable of remaining fast for a longer period than that through the four or five washings normally expected of semipermanent colors. Obviously, the practitioner may elect to vary the technique of any of the three processes described above, e.g., by fixing the treated hair in a desired configuration prior to drying or otherwise may elect to modify the hair coloring compositions disclosed herein with optional additives without departing from the scope of this invention.

The invention will now be further illustrated by, but is not intended to be limited by, the following examples. The quantities of all ingredients are given in per cent, by weight, of the total formulation, unless specified otherwise. In each example, the intensity of the coloration of the test sample was estimated visually by comparison with a control.

EXAMPLE I

This example illustrates the three step process for coloring hair using a cationic salt of a copolymer of an aminoalkyl ester of an ethylenically unsaturated carboxylic acid and a hydroxyalkyl ester of the same acid, as the cationic polymer component, and F. D. and C. Violet 1, (C. I. No. 42640), as the dye component, in accordance with this invention.

The cationic polymer used herein was the phosphate salt of poly(aminoethyl acrylate-hydroxypropyl acrylate) prepared by the method taught in Example I of assignee's U.S. Pat. No. 3,372,149, using phosphoric acid instead of hydrochloric acid. The copolymer was prepared using 75 mole per cent of acrylic acid and 25 mole per cent of hydroxypropyl acrylate.

Part A - An aqueous solution comprising 0.50 per cent, by weight, of the total solution of the above described polyelectrolyte in distilled water was prepared.

Part B - An aqueous solution comprising 0.25 per cent, by weight, of the total solution of the aforementioned dye in distilled water was prepared.

The hair coloring process was carried out as follows:

Step I - A swatch of bleached blond, European hair about 5 inches long and weighing approximately 1 gram was immersed in the above described polymer solution for 5 minutes.

Step II - The swatch of hair was removed from the polyelectrolyte solution bath, and the excess solution was squeezed therefrom by firmly drawing the soaked swatch between the fingers. Said swatch was then rinsed with a stream of tepid (about 110°F.) tap water over a period of 30 seconds.

Step III - The rinsed swatch of hair was then immersed for 5 minutes in a bath containing the above described dye solution. Upon being removed from the dye bath, the swatch was firmly drawn between two fingers and then again rinsed with tap water over a period of about 30 seconds to remove the excess dye. Thereafter the swatch was suspended by a clip fastened at one end and allowed to dry.

When the thoroughly dried test swatch was compared with a similarly dyed control swatch which had not been previously treated with a cationic polymer solution, it was observed that the resultant coloration of the test swatch was considerably more intense than that of the control swatch. The dried test swatch showed improved resistance to "rub-off" and also improved fastness to washing.

EXAMPLE II

This example further illustrates the three step process for coloring hair, using a salt of a poly(aminoalkyl ester of an ethylenically unsaturated carboxylic acid homopolymer), as the cationic polymer, and F. D. and C. Violet 1 (C. I. No. 42640), as the dye, in accordance with this invention.

In this case, said cationic polymer was the phosphate salt of poly(aminoethyl acrylate) prepared by the method taught in Example I of assignee's U.S. Pat. No. 3,372,149, using phosphoric acid in lieu of hydrochloric acid.

The procedural steps I thru III set forth in Example I hereinabove were repeated, using a swatch of bleached blond European hair and the above described cationic polymer and dye in aqueous solutions at concentrations which were the same as those respectively employed in Parts A and B of Example I, supra.

When the present thoroughly dried swatch was compared with a similarly dyed control swatch which had not been previously treated with a cationic polymer solution, it was observed that the resultant coloration of the test swatch was yet more intense than that of the control swatch. In fact, the coloration of the present test sample showed a marked improvement over that of the test sample in Example I hereinabove.

EXAMPLES III — X

These examples further illustrate the three step process for coloring hair, using various acid type dyes with a cationic salt of a copolymer of an aminoalkyl ester of an ethylenically unsaturated carboxylic acid and a hydroxyalkyl ester of the same acid, in one of two series, and with a salt of an aminoalkyl ester of an ethylenically unsaturated carboxylic acid homopolymer in the other.

The cationic polymers used herein were the phosphate salt of poly(aminoethyl acrylate-hydroxypropyl acrylate) which was essentially the same as that employed in Example I hereinabove and the phosphate salt of poly(aminoethyl acrylate) which was essentially the same as that employed in Example II, supra. Each of said salts was utilized in an aqueous solution comprising 0.50 per cent, by weight, of the total solution of the particular polyelectrolyte in distilled water.

Throughout both series, the procedural steps I thru III set forth in Example I hereinabove were repeated, using, in each case, a swatch of bleached blond European hair, either one of the aforementioned cationic polymer solutions, and an aqueous solution comprising 0.25 per cent, by weight, of the total solution of the particular dye in distilled water. A common control swatch, which had been immersed in distilled water for 5 minutes prior to being similarly treated with the respective dye solution, was prepared in each case. The dyes used and the comparative evaluations of the test samples and the controls are set forth below.

| Sample No. | Dye Color Index | Cationic Polymer/Coloration Intensity | | |
|---|---|---|---|---|
| | | Control | Phosphate salt of poly(aminoethyl acrylate-hydroxypropyl acrylate) | Phosphate salt of poly(aminoethyl acrylate |
| III | Acid Blue 7 (42080) | Very light | Medium | Very deep |
| IV | F. D. & C. Yellow 5 (19140) | Very light | Medium | Very deep |
| V | Acid Yellow 23 (19140) | Very light | Medium | Medium |
| VI | Acid Orange 7 (15510) | Very light | Medium | Very deep |
| VII | Noir Acide Brilliant W 759 | Very light | Medium | Very deep |
| VIII | Acid Red 73 (27290) | Very light | Deep | Medium |
| IX | Acid Orange | Very light | Medium | Medium |
| X | Acid Blue 1 (42045) | Very light | Medium | Medium |

The data summarized above clearly illustrate the usefulness of the various dyes with a water-soluble cationic polymer in the hair coloring process in accordance with this invention. Furthermore, the ability of the cationic polymers to impart the desired improved dye receptivity properties to the hair is evidenced by the outstanding results consistently displayed by the test samples throughout the series.

EXAMPLE XI

This example illustrates the two step process for coloring hair using a variety of acid type dyes with a cationic salt of an aminoalkyl ester of a copolymer of an ethylenically unsaturated carboxylic acid and a hydroxyalkyl ester of the same acid in one of two series and with a polyaminoalkyl ester of an ethylenically unsaturated carboxylic acid homopolymer in the other.

The cationic polymers used herein were the phosphate salt of poly(aminoethyl) acrylate-hydroxypropyl acrylate) similar to that employed in Example I, supra, and the phosphate salt of poly(aminoethyl acrylate) similar to that employed in Example II hereinabove. A series of eight aqueous solutions of each of these polyelectrolytes was then prepared as described above in Part A of Example I.

The eight dyes used in the present series were the same as those employed in Examples III thru X hereinabove. Aqueous solutions of each of these dyes were prepared as described above in Part B of Example I to be utilized in the manner set forth below.

Swatches of bleached blond European hair similar to that described in Step I of Example I, supra, were again used as the substrates. Using said swatches and the above described aqueous cationic polymer solutions and dye solutions in the respective order in which they were prepared, the hair coloring process herein was carried out by repeating the procedural steps set forth in Example I hereinabove, except the rinsing operation of Step II was omitted.

When the resulting dried test swatches were compared with respective controls prepared in the same manner as and similar to those described above in Example III – X, they displayed considerably more intense colorations which were comparable to those of the test samples in the preceding examples.

EXAMPLE XII – XVI

These examples illustrate the one step process for coloring hair and the effectiveness of the hair coloring compositions embodied therein, using an aqueous solution of a cationic polymer in combination with an acid type dye, in accordance with this invention.

In each case in the present series of five hair coloring compositions, XII – XVI, a salt of a copolymer similar to that employed in Example I hereinabove was used at a varied concentration as the cationic polymer. Each composition was prepared by merely adding the particular dye and then the cationic polymer to a 200 milliliter beaker containing the amount of distilled water called for. Thereafter the contents of the beaker were moderatley stirred until a homogeneous solution was obtained. The respective formulations of said compositions were as follows:

| Ingredient | Sample No. | | | | |
|---|---|---|---|---|---|
| | XII | XIII | XIV | XV | XVI |
| Benzyl Violet 4B (42640) | 0.1 | 0.01 | — | — | — |
| Erythrosine (45430) | — | — | 0.1 | — | — |
| Brilliant Blue FCF (42090) | — | — | — | 0.1 | 0.05 |
| Phosphate salt of poly-(aminoethyl acrylate-hydroxypropyl acrylate) | 0.5 | 1.0 | 1.0 | 1.0 | 0.5 |
| Distilled Water | 99.4 | 98.99 | 98.9 | 98.9 | 99.45 |

In each case, the hair coloring process was carried out by simply immerging a swatch of bleached blond European hair similar to that employed in Example I hereinabove in one of the above described solutions for approximatey five minutes and then thoroughly rinsing the swatch with tepid (about 110°F) tap water prior to drying.

When compared with a corresponding control swatch which had been immersed in an aqueous solution of the respective dye alone for five minutes, rinsed, and then dried, each of the test swatches herein displayed considerably more intense colorations.

EXAMPLE XVII

This example further illustrates the two step process for coloring hair using a variety of cationic polymers as later defined to prepare the dyeing solutions.

The preparations of the dyeing solutions, the dyeing process and evaluation are carried out essentially as described in Example XI. The dye in all instances is Erythrosine (45430) used at 0.1%, by weight. The cationic polymers (used at a concentration of 0.5%, by weight) are as follows:

| | Polymer | Monomer proportions mole percent |
|---|---|---|
| [A] | Hydrochloride salt of poly(aminoethyl acrylate/acrylamide) | 30/70 |
| [B] | Phosphate salt of poly(aminoethyl acrylate/aminoethyl crotonate) | 95/5 |
| [C] | Hydrochloride salt of poly(aminoethyl methacrylate) | 100 |
| [D] | Phosphate salt of poly(2-aminopropyl acrylate/diethyl fumarate) | 75/25 |
| [E] | Phosphate salt of poly(aminoethyl acrylate/acrylamide/hydroxypropyl acrylate) | 80/4/16 |
| [F] | Phosphate salt of poly(aminoethyl acrylate/diethyl fumarate) | 85/15 |
| [G] | Phosphate salt of poly(aminoethyl maleate/vinyl methyl ether) | 50/50 |
| [H] | Phosphate salt of poly(N-ethyl aminoethyl methacrylate/dioctyl fumarate) | 80/20 |
| [I] | Sulfuric acid salt of poly(aminoethyl acrylate/monomethyl maleate) | 80/20 |
| [J] | Sulfuric acid salt of poly(N-methyl aminoethyl acrylate/ethyl acrylate) | 70/30 |
| [K] | Phosphate salt of poly(aminoethyl methacrylate/dodecyl methacrylate) | 80/20 |
| [L] | Hydrochloride salt of poly(aminoethyl acrylate/vinyl acetate) | 80/20 |
| [M] | Phosphate salt of poly(t-butyl aminoethyl methacrylate/hydroxyethyl acrylate/acrylamide) | 25/25/50 |

All test swatches herein display significantly improved colorations as compared to a corresponding control swatch which is immersed in a solution of the dye alone.

Summarizing, it is thus seen that this invention provides a novel method for coloring hair and hair coloring compositions. Moreover, this invention provides an efficient and economical means for coloring hair and hair coloring compositions, utilizing semipermanent colorants which are void of any irritants and capable of remaining fast for longer than usual periods.

Variations may be made in proportions, procedures, and materials without departing from the scope of this invention which is defined by the following claims.

We claim:

1. A process for coloring hair comprising applying to the hair in effective amount an aqueous solution containing from 0.01 to 1.0 per cent, by weight, of an acid dye in the presence of an aqueous solution containing from 0.1 to 10.0 per cent, by weight, of a water-soluble acid salt of a cationic polymer selected from the group consisting of aminoalkyl esters of (a) a homopolymer of a homopolymerizable unsaturated carboxylic acid having 3 to 5 carbon atoms, (b) a copolymer of a copolymerizable mixture of said unsaturated carboxylic acids, and (c) a copolymer of an unsaturated carboxylic acid having 3 to 5 carbon atoms and at least one copolymerizable ethylenically unsaturated comonomer selected from the group consisting of vinyl acetate, vinyl propionate, vinyl methyl ether, vinyl ethyl ether, the $C_1 - C_8$ alkyl esters and $C_1 - C_8$ alkyl half esters of maleic and fumaric acid, acrylamide, N-methyl acrylamide, methacrylamide and the $C_1 - C_{18}$ alkyl and $C_2 - C_4$ hydroxyalkyl esters of acrylic and methacrylic acids, wherein the copolymer of group (c) contains at least 25 mole per cent of the unsaturated carboxylic acid, and wherein the dye solution and polymer solution are applied together or separately with the application of the polymer solution preceding the application of the dye solution; and thereafter rinsing the hair.

2. A process for coloring hair comprising the steps of:
   A. applying to the hair an effective amount of an aqueous solution containing from 0.1 to 10 per cent, by weight, of a water-soluble acid salt of a cationic polymer selected from the group consisting of aminoalkyl esters of (a) a homopolymer of a homopolymerizable unsaturated carboxylic acid having 3 to 5 carbon atoms, (b) a copolymer of a copolymerizable mixture of said unsaturated carboxylic acids, and (c) a copolymer of an unsaturated carboxylic acid having 3 to 5 carbon atoms and at least one copolymerizable ethylenically unsaturated comonomer selected from the group consisting of vinyl acetate, vinyl propionate, vinyl methyl ether, vinyl ethyl ether, the $C_1 - C_8$ alkyl esters and $C_1 - C_8$ alkyl half esters of maleic and fumaric acids, acrylamide, N-methyl acrylamide, methacrylamide and the $C_1 - C_{18}$ alkyl and $C_2 - C_4$ hydroxyalkyl esters of acrylic and methacrylic acids, wherein the copolymer of group (c) contains at least 25 mole per cent of the unsaturated carboxylic acid,
   B. optionally rinsing the hair with water, and
   C. applying to the hair an aqueous solution containing from 0.01 to 1.0 per cent, by weight, of an acid dye, and thereafter
   D. rinsing said hair.

3. The process of claim 1 wherein said solutions are applied together.

4. The process of claim 1 wherein said water-soluble acid salt of a cationic polymer is the phosphate salt of poly(aminoethyl acrylate-hydroxypropyl acrylate) and is present in an amount ranging from about 0.3 to 0.8 per cent, by weight, of the total solution, and said dye is present in an amount ranging from about 0.1 to 0.5 per cent, by weight, of the total solution.

5. The process of claim 1 wherein said water-soluble acid salt of a cationic polymer is the phosphate salt of poly(aminoethyl acrylate) and is present in an amount ranging from about 0.3 to 0.8 per cent, by weight, of the total solution, and said dye is present in an amount ranging from about 0.1 to 0.5 per cent, by weight, of the total solution.

6. A hair coloring composition comprising an aqueous solution containing (A) from 0.1 to 10 per cent, by weight, of the total solution of a water soluble acid salt of a cationic polymer selected from the group consisting of aminoalkyl esters of (a) a homopolymer of a homopolymerizable unsaturated carboxylic acid having 3 to 5 carbon atoms, (b) a copolymer of a copolymerizable mixture of said unsaturated carboxylic acids, and (c) a copolymer of an unsaturated carboxylic acid having 3 to 5 carbon atoms and at least one copolymerizable ethylenically unsaturated comonomer selected from the group consisting of vinyl acetate, vinyl propionate, vinyl methyl ether, vinyl ethyl ether, the $C_1 - C_8$ alkyl esters and $C_1 - C_8$ alkyl half esters of maleic and fumaric acids, acrylamide, N-methyl acrylamide, methacrylamide and the $C_1 - C_{18}$ alkyl and $C_2 - C_4$ hydroxyalkyl esters of acrylic and methacrylic acids, wherein the copolymer of group (c) contains at least 25 mole per cent of the unsaturated carboxylic acid, and (B) from 0.01 to 1.0 per cent, by weight, of the total solution of an acid dye.

7. The hair coloring composition of claim 6 wherein said water-soluble acid salt of a cationic polymer is the phosphate salt of poly(aminoethyl acrylate-hydroxypropyl acrylate).

8. The hair coloring composition of claim 6 wherein said water-soluble acid salt of a cationic polymer is the phosphate salt of poly(aminoethyl acrylate).

* * * * *